United States Patent [19]

Rinehart

[11] 4,056,549
[45] Nov. 1, 1977

[54] S-3-METHOXYPHENYL N-ALKYLTHIOLCARBAMATES AND S-3-METHYLTHIOPHENYL N-ALKYLTHIOLCARBAMATES

[75] Inventor: Jay Kent Rinehart, Akron, Ohio

[73] Assignee: PPG Industries, Inc., Pittsburgh, Pa.

[21] Appl. No.: 693,666

[22] Filed: June 7, 1976

[51] Int. Cl.$^2$ .................. C07C 155/00; A01N 9/12
[52] U.S. Cl. ................................ 260/455 A; 424/300
[58] Field of Search .................. 260/455 A; 424/300

[56]  References Cited
FOREIGN PATENT DOCUMENTS 741,552   5/1970   Belgium.
371,921   9/1963   Switzerland ................. 260/455 A

OTHER PUBLICATIONS

J. Org. Chem. Soc., vol. 31, (1966) pp. 3980–3984.
Chem. Abst., vol. 81, (1974) p. 34596m.
Chem. Abst., vol. 69, (1968) p. 2688a.
Chem. Abst., vol. 73, (1970) p. 52854u.

*Primary Examiner*—Delbert R. Phillips
*Attorney, Agent, or Firm*—Robert J. Grassi

[57] ABSTRACT

Novel S-3-methoxyphenyl N-alkylthiolcarbamates such as 3-methoxyphenyl N-methylthiolcarbamates, and S-3-methylthiophenyl N-alkylthiolcarbamates such as 3-methylthiophenyl N-methylthiolcarbamate are disclosed, which are useful to control the plant pest *Pythium ultimum* (Damping Off). Also disclosed are the methods of controlling this plant pest with these compounds.

4 Claims, No Drawings

S-3-METHOXYPHENYL N-ALKYLTHIOLCARBAMATES AND S-3-METHYLTHIOPHENYL N-ALKYLTHIOLCARBAMATES

BACKGROUND OF THE INVENTION

The invention concerns S-substituted phenyl N-alkylthiolcarbamates wherein the substituted phenyl is 3-methoxyphenyl or 3-methylthiophenyl, particularly those in which the alkyl is from one to four carbon atoms. The invention also concerns the control of the plant pest *Pythium ultimum*.

DESCRIPTION OF THE PRIOR ART

Plant pests, such as the fungus of *Pythium ultimum*, continually affect the growth of crops, trees, and other desirable vegetation. One method of controlling plant pests such as fungi is by application of chemicals which affect the fungi. These chemicals are applied to the soil, to the desirable plant, or directly to the fungi itself. Because thousands of species of fungi exist, which differ in tolerance to chemicals, new chemicals must be discovered which are effective to control the deleterious effects of particular fungi.

The prior art shows that certain thiolcarbamates are effective against plant pests. The following patents and references illustrate the different thiolcarbamates claimed to be effective against certain plant pests.

U.S. Pat. Nos. 2,977,209 and 3,265,563 disclose S-phenyl N-alkylthiolcarbamates, S-chlorophenyl N-alkylthiolcarbamates, S-ethoxyphenyl N-allylthiolcarbamate, S-ethoxyphenyl N-alkylthiolcarbamates, S-p-tolyl N-alkylthiolcarbamates, and S-2,4-dimethylphenyl N-alkylthiolcarbamates as herbicides and fungicides. U.S. Pat. No. 3,632,332 discloses S-4-methylbenzyl-N,N-diethylthiocarbamate as a herbicide for rice fields. U.S. Pat. No. 3,301,885 discloses S-substituted phenyl N-alkyl, N-alkoxythiolcarbamates as herbicides, miticides, and insecticides. U.S. Pat. No. 3,687,653 discloses trifluoromethylbenzyl N-alkylthiolcarbamates as herbicides. U.S. Pat. No. 3,046,189 and Canadian 789,575 disclose S-alkyl N-alkylthiocarbamates as nematocides. R. Reimschneider and O. Lorenz, in *Monstsch.*, 84, 518 (1953) describe S-phenyl N,N-dimethylthiolcarbamate, and D. G. Crosby and C. Niemann, *Journal of American Chemical Society*, 76, 4458 (1954) describe S-phenyl N-cyclohexylthiolcarbamate, and S-phenyl N-phenylthiolcarbamate. Netherlands Patent No. 6,606,753 discloses S-phenyl N-trifluoromethylphenylthiocarbamate and S-substituted phenyl N-substituted trifluoromethylphenylthiocarbamates as anthelmintics. M. S. Newman and H. A. Karnes, *Journal of Organic Chemistry*, 31, pages 3980-3983 describe S-β-naphthyl N,N-dimethylthiolcarbamate, S-2-nitrophenyl N,N-dimethylthiolcarbamate, S-3-nitrophenyl N,N-dimethylthiolcarbamate, S-2,4,5-trichlorophenyl N,N-dimethylthiolcarbamate, S-3-trifluoromethylphenyl N,N-dimethylthiolcarbamate, S-2,3,5,6-tetramethylpentyl N,N-dimethylthiolcarbamate, S-4-tertbutylphenyl N,N-dimethylthiolcarbamate, S-2-methoxyphenyl N,N-dimethylthiolcarbamate, and S-4-methoxyphenyl N,N-dimethylthiolcarbamate. U.S. Pat. No. 3,932,632 discloses insecticides of dithiophosphate compounds mixed with S-aryl N,N-dialkylthiolcarbamates, or S-aryl N,N-dialkylenethiolcarbamates, or S-aryl, N,N-dialkynylthiolcarbamates, or S-aryl N,N-(alkyl, alkylene, or alkynyl), (alkyl, alkylene, or alkynyl)thiolcarbamates where the aryl may be a substituted phenyl.

SUMMARY OF THE INVENTION

The invention concerns novel substituted phenylthiolcarbamates of the general formula:

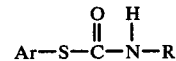

wherein:
Ar is selected from the group consisting of 3-methoxyphenyl and 3-methylthiophenyl; and
R is an alkyl of from one to four carbon atoms.
The invention also concerns the method of controlling the plant pest *Pythium ultimum*.

DESCRIPTION OF THE PREFERRED EMBODIMENTS

The S-substituted phenyl N-alkylthiolcarbamates are represented by the general graphic formula:

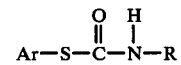

wherein:
Ar is a substituted phenyl of 3-methoxyphenyl, and 3-methylthiophenyl; and
R is an alkyl of from one to four carbon atoms.
The phrase "an alkyl of from one to four carbon atoms" as used herein and in the claims refers to:
methyl, ethyl, n-propyl, isopropyl, n-butyl, sec-butyl, isobutyl, and tert-butyl.

The novel compounds in which Ar is any of the substituted phenyls mentioned herein, and R is an alkyl of from one to four carbon atoms mentioned herein are:
S-3-methoxyphenyl N-methylthiolcarbamate;
S-3-methoxyphenyl N-ethylthiolcarbamate;
S-3-methoxyphenyl N-n-propylthiolcarbamate;
S-3-methoxyphenyl N-isopropylthiolcarbamate;
S-3-methoxyphenyl N-n-butylthiolcarbamate;
S-3-methoxyphenyl N-sec-butylthiolcarbamate;
S-3-methoxyphenyl N-isobutylthiolcarbamate;
S-3-methoxyphenyl N-tert-butylthiolcarbamate;
S-3-methylthiophenyl N-methylthiolcarbamate;
S-3-methylthiophenyl N-ethylthiolcarbamate;
S-3-methylthiophenyl N-n-propylthiolcarbamate;
S-3-methylthiophenyl N-isopropylthiolcarbamate;
S-3-methylthiophenyl N-n-butylthiolcarbamate;
S-3-methylthiophenyl N-sec-butylthiolcarbamate;
S-3-methylthiophenyl N-isobutylthiolcarbamate; and
S-3-methylthiophenyl N-tert-butylthiolcarbamate.

Of these compounds, those in which R is methyl, ethyl, n-propyl, and isopropyl are preferred, and especially preferred are S-3-methoxyphenyl N-methylthiolcarbamate and S-3-methylthiophenyl N-methylthiolcarbamate.

SYNTHESIS OF THE COMPOUNDS a. Synthesis Routes

The compounds may be synthesized by the following routes:

1. Reaction of substituted phenylthiols of the general formula ArSH with the appropriate isocyanates of the general formula RNCO, wherein Ar and R have the same significance as mentioned hereinbefore.

2. Reaction of a substituted phenyl thiolchloroformate of the general formula

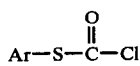

with an amine of the general formula

wherein Ar and R have the same significance as defined hereinbefore.

3. Reaction of a substituted phenylthiol of the general formula ArSH with a carbamoyl chloride of the general formula

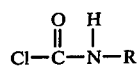

wherein Ar and R have the same significance as defined hereinbefore.

b. Synthesis by Reaction of Substituted Phenylthiol and an Isocyanate

The following example illustrates the synthesis of the compounds by reaction of a substituted phenylthiol with the appropriate isocyanate.

EXAMPLE I

S-3-methoxyphenyl N-methylthiolcarbamate

Methylisocyanate (2.2 grams, 39 millimoles) in anhydrous ethylether (10 milliliters) was slowly added (20 minutes) to a stirred mixture of 3-methoxybenzenethiol (5.0 grams, 36 millimoles) and triethylamine (one to two drops) in anhydrous ethylether (50 milliliters). The clear reaction mixture was refluxed for four hours, and the ethylether solvent was allowed to evaporate off.

A crystalline material (6.9 grams, 95.7 percent yield) was obtained, which was recrystallized from benzene (100 milliliters) to yield 5.4 grams of white crystals of S-3-methoxyphenyl N-methylthiolcarbamate. The crystals had a melting point of 85.5°–88° Centigrade, and an infrared spectrum with a N-H band at 3280 centimeters$^{-1}$ and a C=O band at 1650 centimeters$^{-1}$.

Analysis for: $C_9H_{11}NO_2S$: Calculated: C, 54.80; H, 5.62; N, 7.10. Found: C, 54.89, 54.70; H, 5.39, 5.30; N, 6.93.

Other inert solvents which dissolve the reactants and products and which are easily removed from the products by evaporation, drying, filtering, or washing, and which have a boiling point appropriate to the reaction temperature may be used in lieu of ethylether or benzene, such as tetrahydrofuran, hexane, and chloroform. The reaction temperature may vary from 0° C. to the boiling point of the refluxing mixture. Preferably the reaction temperature range is from 0° C. to 80° C.

c. Synthesis By Reaction of Substituted Phenylthiolchloroformates and Alkylamines The substituted phenylthiolchloroformates are formed from phosgene and the appropriate substituted phenylthiol. U.S. Pat. No. 3,165,544 describes one method of synthesizing these thiolchloroformates.

The following procedure is used to synthesize the compounds disclosed herein by the reaction of the appropriate thiolchloroformate and alkylamine.

A solution containing a substituted phenylthiolchloroformate of the general formula

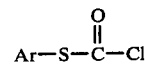

mentioned herein (45 millimoles) e.g., (3-methylthiobenzenethiolchloroformate) in about 10 milliliters of ethylether is slowly added dropwise over a 20 minute period to a vigorously stirred amine solution. The amine solution contains about 100 milliliters of water, 100 milliliters of ethylether, 45 millimoles of triethylamine and about 45 millimoles of an alkylamine of the general formula

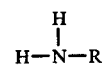

mentioned herein, e.g., ethylamine.

The reaction mixture is stirred for an additional half hour at ambient temperature, and the layers of solution are separated. The aqueous layer is washed once with about 100 milliliters of ethylether, and this ethylether washing and the ethylether layer of the solution are combined. The combined layers are washed with about 100 milliliters of aqueous solutions of 10 weight percent sodium hydroxide, and 10 weight percent hydrochloric acid, respectively, and then dried with anhydrous sodium sulfate ($Na_2SO_4$).

After filtering off the sodium sulfate, the ethylether solvent is removed by evaporation, and the impure S-substituted phenyl N-alkylthiolcarbamate, e.g., S-3-methylthiophenyl N-ethylthiolcarbamate remaining is recrystallized from an inert solvent such as benzene.

d. Synthesis By Reaction of Substituted Phenylthiols With the Appropriate Carbamoyl Chloride The following procedure illustrates synthesis of the compounds mentioned herein, by reaction of substituted phenylthiols of the general formula ArSH mentioned herein with the appropriate alkylcarbamoyl chloride of the general formula

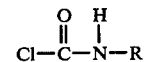

mentioned herein.

A 5 milliliter anhydrous ethylether solution of 50 millimoles of the appropriate alkylcarbamoyl chloride, e.g., methylcarbamoyl chloride and a 5 milliliter anhydrous ethylether solution of 50 millimoles of triethylamine are simultaneously added over a 40 minute period at ambient temperature to a stirred 40 milliliter anhydrous ethylether solution of 50 millimoles of substituted phenylthiol, e.g., 3-methylthiobenzenethiol. The reaction mixture is stirred and refluxed for about 2 to 2½ hours, and is cooled to room temperature and poured into about 50 milliliters of distilled water.

The organic layer and aqueous layer are separated from each other. The aqueous layer is extracted with ethylether and the extracts are combined with the organic layer, which is then washed with about 100 milliliters of a 10 weight percent aqueous solution of sodium hydroxide, and then washed with about 100 milliliters of a 10 weight percent aqueous solution of hydrochloric acid, respectively, and then dried with sodium sulfate which is then filtered off.

The solvent of ethylether is removed by evaporation, and the impure S-substituted phenyl N-alkylthiolcarbamate, e.g., S-3-methylthiophenyl N-methylthiolcarbamate is purified by recrystallization or other techniques if necessary.

PROPERTIES

The novel compounds disclosed herein are used to control the deleterious effects of the fungus *Pythium ultimum*.

These useful properties are illustrated by the following test.

CONTROL OF *Pythium ultimum* (Damping Off)

TEST PROCEDURE

Oospores suspensions of *Pythium ultimum*, which have been examined with a haemocytometer for oospore (plus chlamydospore) numbers per milliliter, were blended at the rate of 1000 oospores per gram of dry sterilized soil.

A blend of sterile soil and the test compound (normally added to the soil as a solution) was also made. The chemically treated soil was mixed with the Pythium-inoculated soil and thoroughly mixed in a soil blender, and the mixture was equally divided, and one of the divisions was placed into a container then seeded with sugar beet seeds, water sealed, and placed in a greenhouse, maintained at 50–75 percent humidity, and 70°–80° Fahrenheit, for 2 weeks.

Containers of sterile soil only, sterile soil plus the test compound, and sterile soil plus *Pythium inoculum*, were also seeded with sugar beet seeds and placed in the greenhouse.

Observations were made for 14 days, and the final observation was made on the 14th day after preparing the samples.

Disease severity was determined by comparing the actual count of the surviving plants in Pythium-inoculated soil with the actual count of the surviving plants in sterile soil.

Control effectiveness of the test compound was determined by comparing the actual count of surviving plants in the chemically treated soil with the actual count of surviving plants in the Pythium-inoculated soil.

Each test consisted of at least three replicates.

The control effectiveness is expressed as percent control calculated by the following formula:

% control = $100\% \frac{\text{(total number of surviving plants in treated soil)}}{\text{(total number of surviving plants in untreated soil)}}$ The amount of test chemical applied is expressed as pounds per acre (lb/A) for 6 inch depth of soil.

The test results for the compounds are shown in Table 1. Column 1 of the table gives the example number; column 2 gives the test compound which was synthesized as disclosed herein unless indicated otherwise; column 3 gives the percent control obtained at 50 pounds per acre.

TABLE 1

PERCENT CONTROL OF *Pythium ultimum*

| Ex. No. | Compound Applied | Percent Control of *Pythium ultimum* at 50 Pounds Per Acre |
|---|---|---|
| II | S-phenyl N-methylthiolcarbamate[a] | 0 |
| III | S-3-methoxyphenyl N-methylthiolcarbamate | 71 |
| IV | S-4-methoxyphenyl N,N-dimethylthiolcarbamate[c] | 0 |
| V | S-4-methoxyphenyl N-methylthiolcarbamate | 0 |
| VI | S-phenyl N,N-dimethylthiolcarbamate[b] | 0 |

[a] described in U.S. Pat. Nos. 2,977,209 and 3,265,563 and disclosed as a systemic nematocide in Applicant's copending application, SYSTEMIC NEMATOCIDE, Serial No. 408,775, filed October 23, 1973.
[b] described in U.S. Pat. No. 2,977,209.
[c] described in Journal of Organic Chemistry, 31, pages 3980–3983.

APPLICATION a. Suitable Agricultural Formulations

The compounds disclosed herein may themselves be applied directly to the soil in the vicinity where the deleterious effects of the plant pests are to be controlled. It is, however, preferable to use suitable agricultural formulations which contain other ingredients which enhance application of the compound. These agricultural formulations will generally comprise from 5 percent to 95 percent or more by weight of one or more S-substituted phenyl N-alkyl, of the general formula:

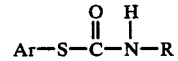

disclosed herein, or mixtures of these compounds, and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

Wettable powders will contain from 25 to 80 percent active ingredients, from 0.1 percent to 5.0 percent wetters and dispersants with the balance consisting of inorganic absorptive diluents.

Since some compounds are solids, others are liquids, and others are viscous materials, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and then the solvent or solvents are evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylated naphthalene.

Granules will contain from 5 percent to 25 percent active ingredients, and may also contain from 1 percent to 20 percent of a surfactant extended upon a granular base such as vermiculite or granular attapulgite. Granules produced by extrusion or tumbling will contain like amounts of active ingredient and surfactant.

b. Combinations With Other Insecticides and Fungicides

For the control of a wider range of crop-pests and diseases it is sometimes desirable to combine one or more of the thiolcarbamates of the general formula:

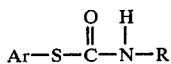

with from 0.05 to 4 parts by weight of insecticides and fungicides, etc., known to be effective against crop-pests and diseases in concentrated premix or during the application step for foliar applications. Examples of other pesticides are: granules containing stable metal azide-metal salt formulations disclosed in assignee's copending application entitled AZIDE-METAL SALT FORMULATIONS, Ser. No. 624,357, filed Oct. 21, 1975, containing S-4-methoxyphenyl N-2,3-dibromopropylthiolcarbamate, disclosed in assignee's copending application entitled S-p-METHOXYPHENYL N-BIS-2,3-DIBROMOPROPYLTHIOLCARBAMATE, Ser. No. 631,751, filed Nov. 7, 1975, or S-4-methoxyphenyl N,N-bis(2,3-dibromopropyl)thiolcarbamate disclosed in assignee's copending application entitled S-p-METHOXYPHENYL N,N-DIALLYLTHIOLCARBAMATE and S-p-METHOXYPHENYL N,N-BIS(2,3-DIBROMOPROPYL)THIOLCARBAMATE, Ser. No. 631,802, filed Nov. 7, 1975, Sevin l(naphthyl-N-methylcarbamate), Chlorobenzilate (ethyl 4,4'-dichlorobenzilate), Guthion (O,O-diethyl-S-[4-oxo-1,2,3-benzotriazin-3(4H)-ylmethyl]phosphorodithioate), Disyston (O,O-diethyl-S-[2-(ethylsulfinyl)ethyl]phosphorodithioate), Maneb (manganous ethylene bisdithiocarbamate), Karathane (mixture of 2,4-dinitro-6-octylphenylcrotonate, 2,6-dinitro-4-octylphenylcrotonate, nitrooctylphenols (principally dinitro), 4-(1-methylheptyl)2,6-dinitrophenylcrotonate, 4-(1-ethylhexyl)2,6-dinitrophenylcrotonate, 4-(1-propylpentyl)2,6-dinitrophenylcrotonate, 6-(1-methylheptyl)-2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzensulfonate), Benlate (methyl 1-(butylcarbamoyl)-2-benzimidazolecarbamate), or Plantvax (5,6-dihydro-2-methyl-1,4-oxathiin-3-carboxanilide-4,4-dioxide).

In some instances it is also desirable to include special purpose additives which will inhibit corrosion, reduce foaming, reduce caking, or increase flocculation.

The following example illustrates a suitable emulsifiable concentrate formulation, for dilution in water for spraying plants, particularly, plant foliage or for application to other plant parts as herein mentioned. In this emulsifiable concentrate formulation, the percentages are weight percent.

EXAMPLE VII

EMULSIFIABLE CONCENTRATE FORMULATIONS

| | |
|---|---|
| 3-methoxyphenyl N-methylthiolcarbamate | 13% |
| Xylene | 41% |
| Isophorone | 41% |
| Atlox ® 3404* | 1% |
| Atlox ® 3403 F* | 4% |

*Commercial emulsifier for agricultural pesticides manufactured by Atlas Powder Co., Wilmington, Delaware, and registered with the U.S. Food and Drug Administration.

c. Amount of the Compounds Described Herein to Apply

The novel compounds described herein when used for a fungicide, to control plant pests, particularly the soil fungus *Pythium ultimum* (Damping Off), are applied in an amount effective to control this plant pest. This amount is a fungicidal amount, which amount will vary with the season of the year, the weather, and the severity of the disease. The fungus include those specifically described and shown herein as well as equivalent species which are biologically related such as those of the genus Pythium and are controlled by application of the compounds.

A single compound may be used in the formulation described herein, preferably a plurality of the compounds are used together either in a formulation or by concurrent application, that is applying one or more of the compounds to the soil itself. In other applications, one or more compounds may be applied to the soil, and within about 10 days, the same compound, or one or more different compounds may be applied to the soil so as to effectively control the plant pests.

When used to control the soil fungus *Pythium ultimum* the novel compounds may be applied at rates of from 6 pounds per acre per 6 inch depth of soil to as high as 500 pounds per acre per 6 inch depth of soil, depending upon, the application method, e.g., soil incorporation, discing, band, the type of formulation used, the plant species to be protected, the extent of the soil infestation, local conditions such as temperature, humidity, moisture content of the soil, nature of the soil, e.g., clay, loam, sand, pH, etc.

Those compounds in which R is methyl, ethyl, n-propyl, or isopropyl may be used at lower rates such as from 6 pounds per acre to 300 pounds per acre, of these compounds those in which R is methyl may be used at lower rates of 12 pounds per acre to 200 pounds per acre, and those in which Ar is 3-methoxyphenyl are generally used at the lowest rates of 12 pounds per acre to 150 pounds per acre while the compound S-3-methoxyphenyl N-methylthiolcarbamate itself may be used at 12 pounds to 75 pounds per acre per 6 inch depth of soil. Preferably the compound is applied prior to planting the plants.

The phrase "to effectively control the deleterious effects of plant pest" as used herein and in the claims means that control required to increase the yield of plants growing in infested areas and treated with the compound, as compared to non-treated plants. This effective control may range from 10 percent to 100 percent control.

The phrase "applying an effective amount" as used herein and in the claims means applying that amount necessary to attain effective control by any application technique in which the compound and plant pest are brought into mutual contact, such as to the foliage of the plant, to the soil itself, to the fungus itself, or other plant pest. Generally, application to the soil itself is preferred, that is the compound is applied directly to the soil and disced or plowed, or mixed with the soil, generally before the plants are planted. It is also possible in some cases to apply the compound to the soil after the plants have been affected by the plant pest.

d. Application To Control Other Plant Pests

Although the novel compounds of the general formula

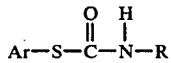

are used to control *Pythium ultimum,* this does not preclude their use against other plant pests such as weeds or fungus.

For example, those compounds in which Ar is 3-methoxyphenyl and R is an alkyl mentioned herein, can be used at rates from 50 to 500 pounds per acre per 6 inch depth of soil to control the plant pest of the fungus *Fusarium solani.*

While the invention has been described with reference to specific details of certain illustrative embodiments, it is not intended that it shall be limited thereby except insofar as such details appear in the accompanying claims.

I claim:

1. A S-substituted phenyl N-alkylthiolcarbamate represented by the general formula:

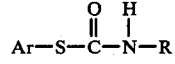

wherein:
   Ar is selected from the group consisting of 3-methoxyphenyl and 3-methylthiophenyl; and
   R is an alkyl of from one to four carbon atoms.

2. The thiolcarbamate of claim 1, wherein R is selected from the group consisting of methyl, ethyl, n-propyl, and isopropyl.

3. 3-Methoxyphenyl N-methylthiolcarbamate.

4. 3-Methylthiophenyl N-methylthiolcarbamate.

* * * * *